United States Patent
Cantor et al.

(10) Patent No.: US 9,376,714 B2
(45) Date of Patent: *Jun. 28, 2016

(54) METHOD FOR DETECTING AND QUANTIFYING RARE MUTATIONS/POLYMORPHISMS

(75) Inventors: Charles R Cantor, Del Mar, CA (US); Chunming Ding, Singapore (SG)

(73) Assignee: Trustees of Boston University, Boston, MA (US)

( * ) Notice: Subject to any disclaimer, the term of this patent is extended or adjusted under 35 U.S.C. 154(b) by 69 days.

This patent is subject to a terminal disclaimer.

(21) Appl. No.: 13/412,984

(22) Filed: Mar. 6, 2012

(65) Prior Publication Data

US 2012/0156685 A1 Jun. 21, 2012

Related U.S. Application Data

(63) Continuation of application No. 12/496,390, filed on Jul. 1, 2009, now Pat. No. 8,153,377, which is a continuation of application No. 10/589,709, filed as application No. PCT/US2005/005255 on Feb. 18, 2005, now Pat. No. 7,709,262.

(60) Provisional application No. 60/545,382, filed on Feb. 18, 2004.

(51) Int. Cl.
    C12Q 1/68 (2006.01)

(52) U.S. Cl.
    CPC ........ *C12Q 1/6827* (2013.01); *C12Q 2600/156* (2013.01)

(58) Field of Classification Search
    None
    See application file for complete search history.

(56) References Cited

U.S. PATENT DOCUMENTS

| 5,639,606 A | 6/1997 | Willey |
| 5,643,765 A | 7/1997 | Willey |
| 5,714,320 A | 2/1998 | Kool |
| 5,876,978 A | 3/1999 | Willey et al. |

(Continued)

FOREIGN PATENT DOCUMENTS

| WO | 9630545 A1 | 10/1996 |
| WO | 9828440 A1 | 7/1998 |

(Continued)

OTHER PUBLICATIONS

Fan et al. Parallel genotyping of human SNPs using generic high-density oligonucleotide tag arrays. Genome Research 10:853-860 (2000).

(Continued)

*Primary Examiner* — Samuel Woolwine
(74) *Attorney, Agent, or Firm* — Nixon Peabody LLP; Ronald I. Eisenstein; Leena H. Karttunen Contarino

(57) ABSTRACT

The present invention is directed to a method for detecting and quantifying rare mutations in a nucleic acid sample. The nucleic acid molecules under investigation can be either DNA or RNA. The rare mutation can be any type of functional or non-functional nucleic acid change or mutation, such as deletion, insertion, translocation, inversion, one or more base substitution or polymorphism. Therefore, the methods of the present invention are useful in detection of rare mutations in, for example, diagnostic, prognostic and follow-up applications, when the targets are rare known nucleic acid variants mixed in with the wildtype or the more common nucleic acid variant(s).

8 Claims, 5 Drawing Sheets

(56) References Cited

U.S. PATENT DOCUMENTS

| | | | |
|---|---|---|---|
| 6,013,431 | A | 1/2000 | Söderlund et al. |
| 6,297,017 | B1 | 10/2001 | Schmidt et al. |
| 6,972,174 | B2 | 12/2005 | Xue et al. |
| 7,041,447 | B2 | 5/2006 | Evans et al. |
| 7,655,399 | B2 | 2/2010 | Cantor |
| 7,700,225 | B2 | 4/2010 | Cantor |
| 7,785,798 | B2 | 8/2010 | Cantor |
| 8,034,567 | B2 | 10/2011 | Cantor |
| 2002/0025532 | A1 | 2/2002 | Huang et al. |
| 2002/0081598 | A1 | 6/2002 | Evans et al. |
| 2003/0017487 | A1 | 1/2003 | Xue et al. |
| 2004/0224331 | A1 | 11/2004 | Cantor |
| 2007/0122805 | A1 | 5/2007 | Cantor |
| 2007/0207466 | A1 | 9/2007 | Cantor et al. |
| 2011/0244451 | A1 | 10/2011 | Cantor |

FOREIGN PATENT DOCUMENTS

| | | |
|---|---|---|
| WO | 00/50869 A2 | 8/2000 |
| WO | 01/42496 A2 | 6/2001 |
| WO | 01/68913 | 9/2001 |
| WO | 01/90399 A2 | 11/2001 |
| WO | 01/96607 A2 | 12/2001 |
| WO | 2004022721 A2 | 3/2004 |

OTHER PUBLICATIONS

Amexis, et al., "Quantitative mutant analysis of viral quasispecies by chip-based matrix-assisted laser desorption/ionization time-of-flight mass spectrometry," PNAS 98(21):12097-12102, 2001.

Amexis, et al., "Sequence diversity of Jeryl Lynn strain of mumps virus: quantitative mutant analysis for vaccine quality control." Virology 300(2):171-179, 2002.

Böcker, "SNP and mutation discover using base-specific cleavage and MALDI-TOF mass spectrometry." Bioinformatics 19(Suppl 1):i44-i53, 2003.

Braun et al., "Improved Analysis of Microsatellites Using Mass Spectrometry." Genomics 46:18-23, 1997.

Buchanan, F. C. et al., "Association of a missense mutation in the bovine leptin gene with carcass fat content and leptin MRNA levels." Genetics Selection Evolution, EDP Sciences, Les Ulis., FR 34(1):105-116, 2002.

Elso et al., "Mutation Detection Using Mass Spectrometric Separation of Tiny Oligonucleotide Fragments." Genome Research 12:1428-1433, 2002.

Lefmann, M. et al., "Novel Mass Spectrometry-Based Tool for Genotypic Identification of Myobacteria" Journal of Clinical Microbiology 42(1):339-346, 2004.

Nasis, O. et al. "Improvement in sensitivity of allele-specific PCR facilitates reliable noninvasive prenatal detection of cystic fibrosis." Clin Chem 50:694-701, 2004.

Sauer et al., "Facile method for automated genotyping of single nucleotide polymorphisms by mass spectrometry." Nucleic Acids Research 30(5):1-5, e22, 2002.

Tang, et al., "Single nucleotide polymorphism analyses by MALDI-TOF MS." International Journal of Mass Spectrometry 226:37-54, 2003.

Landegren, et al., "Reading Bits of Genetic Information: Methods for single-Nucleotide Polymorphism Analysis," Genome Research, vol. 8: 769-776, 1998.

Ding, C. and Cantor, C. R., "A high-throughput gene expression analysis technique using competitive PCR and matrix-assisted laser desorption ionization time-of-flight MS." PNAS 100(6):3059-3064, 2003.

Bernard et al., Nucleic Acids Research 24(8):1435-1442, 1996.

Doris et al., J. Chromatography A May 8;806(1):47-60, 1998.

Gardner et al., Science 301:102-105, 2003.

Holland et al., PNAS 88:7276-7280, 1991.

Maier et al., Ann Neurol. 52:683-688, 2002.

Shalon et al., Genome Research 6(7):639-645, 1996.

Suomalainen et al., Mol. Biotechnol. 15(2):123-131, 2000.

Braun et al. Detecting CFTR gene mutations by using primer oligo base extension and mass spectrometry. Clinical Chemistry, 43(7): 1151-1158 (1997).

QIAquick Spin Handbook (Jul. 2002).

Singer-Sam et al., "A Sensitive, Quantitative Assay for Measurement of Allele-specific Transcripts Differing by a Single Nucleotide", PCR Methods and Applications, vol. 1, No. 3, pp. 160-163, 1992.

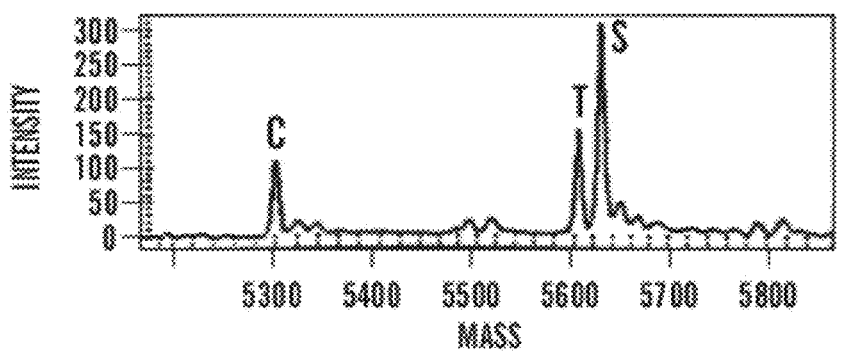
*FIG. 3A*
*FIG. 3B*
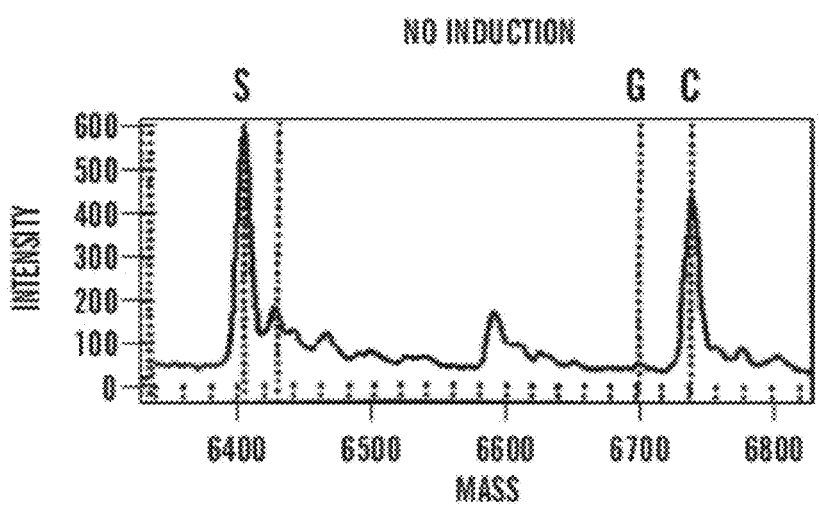
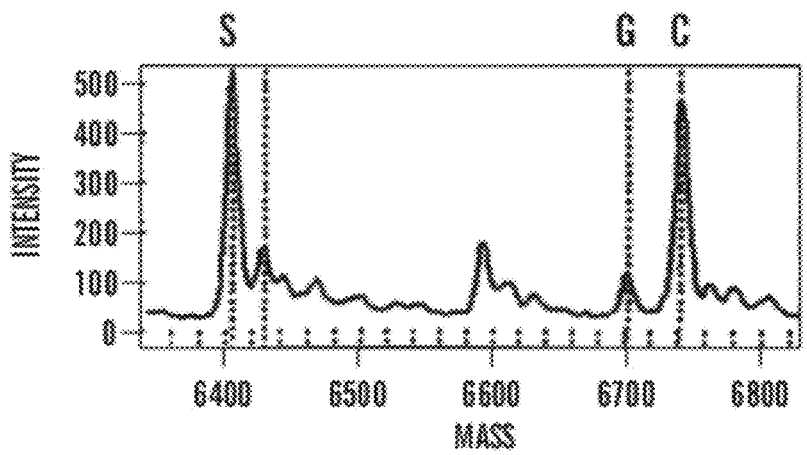

METHOD FOR DETECTING AND QUANTIFYING RARE MUTATIONS/POLYMORPHISMS

CROSS REFERENCE TO RELATED APPLICATIONS

The present application is a continuation application under 35 U.S.C. §120 of U.S. application Ser. No. 12/496,390, filed on Jul. 1, 2009, which is a continuation application under 35 U.S.C. §120 of U.S. application Ser. No. 10/589,709, filed on Apr. 12, 2007, issued as U.S. Pat. No. 7,709,262 on May 4, 2012, which is a 371 National Stage of International Application No. PCT/US2005/005255 filed on Feb. 18, 2005, which designated the U.S., and which claims benefit under 35 U.S.C. §119(e) of U.S. Provisional Application Ser. No. 60/545,382 filed Feb. 18, 2004, the contents of which are herein incorporated by reference in their entirety.

SEQUENCE LISTING

The instant application contains a Sequence Listing which has been submitted via EFS-Web and is hereby incorporated by reference in its entirety. Said ASCII copy, created on Jul. 28, 2010, is named 70158605.txt and is 7,866 bytes in size.

BACKGROUND OF THE INVENTION

The present invention relates to methods of detecting and quantifying rare nucleic acids changes, mutations or polymorphisms in a nucleic acid sample; namely, the sample contains a much smaller percentage of the changed, mutated or polymorphic nucleic acid molecule compared to that of the wildtype or more common variants or control nucleic acid molecules.

Detection of a nucleic acid containing a rare polymorphism or mutation can be problematic. Such problems occur in numerous situations, for example, if a nucleic acid sample is suspected of containing a small population of mutant nucleic acids such as in diagnosis or prognosis of cancer, viral infections, variations in viral infections, such as various HIV strains in the same individual, and the like. In all these cases, it is important to know accurately whether the nucleic acid sample actually contains the rare mutant allele or not, and in many cases it would be helpful to know how much mutant allele containing nucleic acid is present in the sample, particularly in relation to the wildtype or the more common nucleic acid molecule.

Methods for detection and quantification of nucleic acids that contain differences which are present in only low quantities or small percentages compared to a wildtype or control nucleic acid molecule in the sample can be important in many clinical applications. Non-limiting examples of applications wherein detection of rare nucleic acid changes would be useful include early benign or malignant tumor detection, prenatal diagnostics particularly when using a plasma or serum DNA sample from the mother, early viral or bacterial disease detection, environmental monitoring, monitoring of effects of pharmaceutical interventions such as early detection of multi drug resistance mutations in cancer treatment. Also, a number of mutations causing inherited diseases result in reduction of the transcript levels. Therefore, improved methods allowing detection of the mutant transcript which is present at very low levels would allow a simplification of mutation detection, particularly at the RNA level, in cases wherein the mutant transcript levels are low.

Detection of rare mutations could also provide tools for forensic nucleic acid sample analysis by providing a system to reliably detect presence or absence of specific nucleic acid polymorphisms to provide evidence to exonerate a crime suspect.

Additionally, detection of rare mutations in biological agents such as bacteria and viruses that can be used as a biological warfare agents would provide an important tool for detecting spread of harmful biological materials.

Another problem requiring a satisfactory solution is in the commonly used genotyping methods, is a so called "allele dropout"-problem which happens when one allele is poorly amplified or detected and a heterozygotic allele is mis-called as a homozygote. The dropout allele is usually, but not always, the allele that produces a higher molecular weight base extension product. A method which would allow the detection of allele dropout, particularly in clinical diagnostic applications, would be extremely useful and improve the accuracy of distinguishing heterozygotes from homozygotes, which can be crucial for evaluating, for example, disease prognosis.

The methods for mutation detection and nucleic acid molecule quantification have traditionally included Southern-blot and Northern-blot hybridization, ribonuclease protection assay, and polymerase chain reaction (PCR) and reverse transcriptase PCR (RT-PCR) based methods. However, both direct detection methods and PCR-based methods to detect nucleic acid molecules suffer from lack of sensitivity to detect or amplify the rare nucleic acid mutation, when the sample nucleic acid contains both a large amount of the wildtype nucleic acids and a much smaller amount of the rare mutation or polymorphism.

Absolute quantification of nucleic acid molecule copy numbers in a sample is a requirement if one wishes to monitor the number of mutant or polymorphic nucleic acids, for example, at different time points or as a response to a pharmaceutical intervention. However, quantification of nucleic acid copy numbers for rare mutations is difficult using PCR based methods because the common nucleic acid molecule is also amplified exponentially and the mixture of amplified sample almost always contains large amounts of the wildtype or "normal" nucleic acid variant relative to the rare nucleic acid variant.

A number of quantitative PCR based methods have been described including RNA quantification using PCR and complementary DNA (cDNA) arrays (Shalon et al., Genome Research 6(7):639-45, 1996; Bernard et al., Nucleic Acids Research 24(8):1435-42, 1996), solid-phase mini-sequencing technique, which is based upon a primer extension reaction (U.S. Pat. No. 6,013,431, Suomalainen et al. Mol. Biotechnol. June; 15(2):123-31, 2000), ion-pair high-performance liquid chromatography (Doris et al. J. Chromatogr. A May 8; 806(1):47-60, 1998), 5' nuclease assay or real-time RT-PCR (Holland et al. Proc Natl Acad Sci USA 88: 7276-7280, 1991), and real competitive RT-PCR (Ding et al. Proc Natl Acad Sci USA 100:3059-3064, 2003).

Methods using PCR and internal standards differing by length or restriction endonuclease site from the desired target sequence allowing comparison of the standard with the target using gel electrophoretic separation methods followed by densitometric quantification of the target have also been developed (see, e.g., U.S. Pat. Nos. 5,876,978; 5,643,765; and 5,639,606). These methods, also sometimes referred to as StaRT-PCT, have severe limitations in measuring an absolute transcript quantity in a biological sample. Because of the size differences between the standard and the target sequence, the PCR amplification can not be expected to be the same for both the standard and the target sequence. Further, because a separate gel electrophoretic separation and/or restriction endonuclease digestion followed by gel electrophoretic separation, and densitometric measurement are required after amplification, the method has steps which are prone to errors and make the quantification of small amounts of nucleic acids cumbersome.

Therefore, it would be useful to develop a method which allows sensitive and accurate detection and quantification of nucleic acids containing rare changes and which can be easily automated and scaled up to accommodate testing of large numbers of sample and which overcome the sensitivity problems of nucleic acid detection. Such a method would enable diagnosing different pathological conditions, including viruses, bacteria and parasites, as well as different benign and malignant tumors, neurological disorders, heart disease and autoimmune disorders. Such a method would also allow quantifying the rare transcripts of interest for diagnostic, prognostic and therapeutic purposes.

SUMMARY OF THE INVENTION

The present invention is directed to a method for detecting and quantifying rare mutations in a nucleic acid sample. The nucleic acid molecules under investigation can be either DNA or RNA. The rare mutation can be any type of functional or non-functional nucleic acid change or mutation, such as deletion, insertion, translocation, inversion, polymorphism and one or more base substitution. Therefore, the methods of the present invention are useful in detection of rare mutations in, for example, diagnostic, prognostic and follow-up applications, when the targets are rare known nucleic acid variants mixed in with the wildtype or the more common nucleic acid variant(s).

In one embodiment, the invention provides a method of detecting nucleic acids with a rare mutation comprising the steps of amplifying a nucleic acid molecule with at least two primers flanking the mutation site, designing a detection primer so that the 3' end of the detection primer is immediately adjacent to the first nucleic acid which differentiates the wildtype nucleic acid variant from the mutant nucleic acid variant molecule, removing the excess dNTPs after the amplification reaction, performing a primer extension reaction using the detection primer and at least one dNTP or ddNTP, which corresponds to a nucleoside adjacent to the detection primer in the rare mutant nucleic acid molecule, wherein the presence of a primer extension product in the reaction indicates the presence of the nucleic acid with a rare mutation. In the preferred embodiment, only one dNTP or ddNTP is used. However, so long as the primer is designed so that the background wildtype or the more common nucleic acid molecule(s) cannot serve as a template, more than one dNTP/ddNTP can be used in the primer extension reaction.

In one embodiment, the invention provides a method, wherein only one dNTP, which corresponds to the nucleotide adjacent to the detection primer in the rare mutant nucleic acid molecule is used together with the detection primer.

In another embodiment, the invention provides a method of detection of nucleic acid molecules with a rare mutation comprising amplifying the nucleic acid sample with two primers that are designed to allele-specifically amplify the rare mutation containing nucleic acid, removing the excess dNTPs from the reaction after the amplification reaction, performing the primer extension reaction with at least one dNTP or ddNTP, preferably dNTP, and a detection primer, which has been designed so that the 3' end is immediately adjacent to the mutation site, so that only the mutant nucleic acid will serve as a template to the primer extension reaction when the corresponding dNTP or ddNTP is used, and detecting the primer extension reaction product, wherein presence of the primer extension product after the primer extension reaction indicates the presence of a nucleic acid with a rare mutation.

In one embodiment, two reactions are performed using two different detection primers, wherein the first detection primer is designed to amplify the sense strand so that the 3' end of the primer anneals immediately adjacent to the mutation site in the sense strand and in the second reaction the detection primer is designed to amplify the antisense strand so that the 3' end of the primer anneals immediately adjacent to the mutation site in the antisense strand.

In yet another embodiment, the invention provides a method of quantifying nucleic acid molecules with rare mutations comprising the steps of amplifying a nucleic acid sample and a known amount of a control nucleic acid sample in the same reaction, wherein the control nucleic acid sample has been designed to have the same sequence as the rare mutation containing amplicon with the exception of at least one, 2, 3, 4, 5-10, preferably only one nucleic acid difference immediately adjacent to the mutation site. The amplification is performed with primers flanking the mutation site. After amplification, the excess dNTPs are removed and a primer extension reaction is performed using at least one detection primer, which is designed so that the 3' end of the primer anneals immediately adjacent to the rare mutation site. The detection reaction is performed in the presence of dNTPs and/or ddNTPs. For example, at least one deoxynucleotide (dNTP), corresponding to the mutant nucleoside immediately 3' of the detection primer and two dideoxynucleotides (ddNTPs), which correspond to the nucleoside(s) that differentiate the control from the rare mutant nucleic acid. The primer extension products are then detected, and because the amount of the control originally added to the amplification reaction is known, the ratio of the control and the rare mutant containing nucleic acid molecules is used to determine the exact quantity of the mutant nucleic acid molecules in the sample. Preferably, only one dNTP is used. However, so long as the primer and dNTP/ddNTP combinations are designed so that the more common nucleic acid cannot be amplified in the primer extension reaction, the combination of dNTPs/ddNTPs may vary.

BRIEF DESCRIPTION OF THE FIGURES

FIGS. 1A-1E show quantification of rare mutations. In the absence (FIG. 1A), 20 fold excess (FIG. 1C) and 100 fold excess (FIG. 1D) of wildtype DNA, the ratios of mutant DNA and the competitor DNA are very similar. In FIG. 1B, only 500 fold excess wildtype DNA was present and neither mutant nor competitor DNA was present. In FIG. 1E, 500 fold excess wildtype DNA, mutant DNA and competitor DNA were all present. The sequences of the nucleic acid molecules shown in the FIG. 1 are described in the Example.

DETAILED DESCRIPTION OF THE INVENTION

Figure 1A:
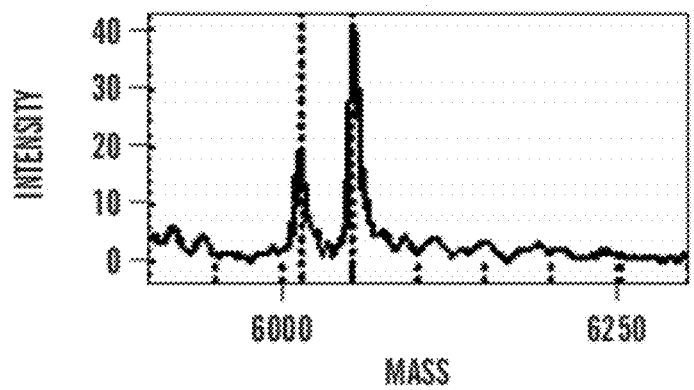

The present invention is directed to a method for detecting and quantifying rare mutations in a biological sample. The sample nucleic acid molecules that can be used in the methods of the present invention include DNA, RNA and cDNA molecules. The present invention provides a method for robustly detecting whether such rare mutations occur in a biological sample.

The term "mutation" as used throughout the specification is intended to encompass any and all types of functional and/or non-functional nucleic acid changes, including mutations and polymorphisms in the target nucleic acid molecule when compared to a wildtype variant of the same nucleic acid region or allele or the more common nucleic acid molecule present on the sample. Such changes, include, but are not limited to deletions, insertions, translocations, inversions, and base substitutions of one or more nucleotides.

As used herein, polymorphism refers to a variation in the sequence of a gene in the genome amongst a population, such as allelic variations and other variations that arise or are observed. Genetic polymorphisms refers to the variant forms of gene sequences that can arise as a result of nucleotide base pair differences, alternative mRNA splicing or post-translational modifications, including, for example, glycosylation. Thus, a polymorphism refers to the occurrence of two or more genetically determined alternative sequences or alleles in a population. These differences can occur in coding and non-coding portions of the genome, and can be manifested or detected as differences in nucleic acid sequences, gene expression, including, for example transcription, processing, translation, transport, protein processing, trafficking, DNA synthesis, expressed proteins, other gene products or products of biochemical pathways or in post-translational modifications and any other differences manifested among members of a population. A single nucleotide polymorphism (SNP) refers to a polymorphism that arises as the result of a single base change, such as an insertion, deletion or change in a base.

A polymorphic marker or site is the locus at which divergence occurs. Such site may be as small as one base pair (an SNP). Polymorphic markers include, but are not limited to, restriction fragment length polymorphisms, variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms may be observed by differences in proteins, protein modifications, RNA expression modification, DNA and RNA methylation, regulatory factors that alter gene expression and DNA replication, and any other manifestation of alterations in genomic nucleic acid or organelle nucleic acids.

The allelic form occurring most frequently in a selected population is sometimes referred to as the wildtype form.

Diploid organisms may be homozygous or heterozygous for allelic forms. A diallelic or biallelic polymorphism has two forms. A triallelic polymorphism has three forms.

The term "rare mutation" as used herein and throughout the specification is intended to describe a mutation in a nucleic acid molecule which is present in less than 40% of the nucleic acid molecules in the sample, preferably in less than 30%, 20%, 15%, 10%, 8%, 5%, 4%, 3%, 2%, 1%, 0.8%, 0.5%, 0.1%, 0.05%, 0.01, or less compared to one or more, more common nucleic acid variants, which are referred to throughout the specification as the "wildtype" nucleic acid variants. In one embodiment, the rare nucleic acid is present in the sample in amount less than 10%, preferably less than 1%. The sample may include one or more rare mutations and there may also be one or more wildtype variants in the nucleic acid sample.

The deoxynucleotides or dNTPs according to the present invention are dATP, dTTP, dCTP, or dGTP. The dideoxynucleotides or the terminator nucleotides (ddNTPs) are ddATP, ddTTP, ddCTP, or ddGTP. The dNTPs and ddNTPs can also be labeled with, for example, different fluorescent dyes, or other labels, such as radioactive molecules, which do not interfere with the DNA polymerase function in the primer extension reaction. Differentially labeled dNTPs or ddNTPs can be used to differentiate the alleles after the primer extension reaction. Such labels and the methods of preparing labeled dNTPs and ddNTPs are well know to one skilled in the art.

The terms "nucleic acid sample", "nucleic acid molecule", or "nucleic acid" as described throughout the specification are intended to encompass nucleic acids isolated from any biological material, e.g., human, animal, plant, bacteria, fungi, protist, viruses, from tissues including blood, hair follicles, or other tissues, such as skin biopsies, cells or cell cultures, body excrements such as semen, saliva, stool, urine, amniotic fluid and so forth. The nucleic acids can also be isolated from foodstuff, drinks, clothes, soil and any other source, wherein detection of rare nucleic acids compared to a more common or wildtype variants of the same is needed. Nucleic acid molecules can be isolated from a particular biological sample using any of a number of procedures, which are well-known in the art, the particular isolation procedure chosen being appropriate for the particular biological sample.

In one embodiment, the invention provides a method of detecting one or more nucleic acids with a rare mutation comprising the steps of amplifying a nucleic acid molecule with two primers flanking or surrounding the mutation site, designing a detection primer so that the 3' end of the detection primer anneals immediately adjacent to a nucleic acid which is different in the mutant molecule compared to the more common wildtype variant of the same nucleic acid molecule, removing the excess dNTPs after the amplification reaction, performing a primer extension reaction using the detection primer and at least one dNTP or ddNTP, which corresponds to the nucleotide adjacent to the detection primer present in the rare mutant nucleic acid molecule and is not present in the background of the more common nucleic acid molecule(s) or variant(s), wherein the presence of a primer extension product in the reaction indicates the presence of the nucleic acid with a rare mutation. Preferably, only one dNTP or ddNTP is used in the primer extension reaction.

In one embodiment, the invention provides a method, wherein only one dNTP, which corresponds to the nucleoside adjacent to the detection primer in the rare mutant nucleic acid molecule is used together with the detection primer.

For example, a nucleic acid molecule contains the following sequence:

[SEQ ID NO: 1]
5'TGGGGCAAGGTGAACGTGGATGAAGTTGGTGGTGAGGCCCTGGGC

AGGTTTaggggcagatagcagtga[A/T]GAGAGCGAGAGAGCCATCT

ATTGCTTACATTTGCTTCTGACACAACTGTGTTCACTAGCAACCTCA

AACAGACACCATGGTGCACCTGACTCCTGAGGAGAAGTCTGCCGTTA

CTGCCCTG3', wherein [A/T] represents a base A to T mutation. T mutation occurs at low frequencies, for example, less than about 30%, 20%, 15%, 10%, 8%, 5%, 4%, 3%, 2%, 1%, 0.8%, 0.5%, 0.1%, 0.05%, 0.01% or less. Therefore, in a biological sample, most nucleic acid molecules for the region depicted above have the A base and only a very small percentage of the nucleic acid molecules present in the biological sample have the T base at the polymorphic site.

To detect the rare mutation, nucleic acids are isolated from the source material, such as tissues/cells/fluids or other sources of interest, using any of the widely adopted methods well known to one skilled in the art. Two PCR primers flanking the mutation site are shown as underlined sequences in the above example, wherein only the sense strand is shown. The primers are designed to amplify the DNA region for both the wildtype and mutant DNAs. To further increase the sensitivity of the method to detect rare known mutations, allele specific primers can be used to preferentially amplify the rare mutation containing nucleic acid molecule(s). After the PCR, the excess nucleotides in the amplification reaction are removed, for example, using a shrimp alkaline phosphatase or a spin column or any other method well known to one skilled in the art. A third primer, so called detection primer, which is shown in the above example in small letters, is used in a base extension reaction. The third primer can also be designed from the opposite direction and the two primers in two parallel reactions can be used to cross-validate the results. It is important that the detection primer is designed so that its 3' end anneals immediately before a nucleoside which is different in the rare mutant(s) compared to more common wildtype nucleic acid variant(s) because the methods of the present invention are based on the premise of preferentially detecting the rare nucleic acid molecules.

In the base extension reaction using the above presented example nucleic acid template, only ddTTP or alternatively, only dTTP is used so that only the mutant nucleic acid will be used as the template for the base extension reaction. The detection of the oligonucleotide resulting from the primer extension reaction, i.e., aggggcagatagcagtga-ddT [SEQ ID NO.: 2] indicates that the mutant allele is present.

Other combinations of ddNTP and dNTP can also be used as far as the wildtype nucleic acid(s) cannot be used as the template for the base extension reaction.

The methods of the present invention can additionally be used to detect more than one rare nucleic acid variant in the sample. For example, a multiplex PCR and a subsequent multiplex primer extension reaction can be designed using the teachings of the present invention to detect at least 2, 3, 4, 5, 6, 7, 8, 9, 10-15 or even more than 15 mutations in the same reaction, as long as none of the wildtype, or more common variants of the respective nucleic acid targets can serve as a template for the detection primers in the primer extension reaction.

The methods of the present invention are useful, for example, in detecting a small population of nucleic acids with a known mutation among a background of wildtype nucleic acid variants in, for example, early diagnosis or prognosis of cancer or malignant cell growth in an individual. The methods of the present invention are also useful in providing a means for early detection of malignant cells containing new or additional mutations which may be a result of treatment of the malignancies, such as appearance of multi drug resistance mutations in an individual with the proviso that these mutations are known or become known through screening of new mutations before designing the detection primers.

The methods of the present invention also provide a useful tool to detect viral infections or emerging virus mutants in an individual infected with a virus, such as human immune deficiency virus (HIV), during the treatment of the disease thereby allowing early adjustment in treatment as a response to occurrence of new virus mutations.

Due to their sensitivity, the methods of the present invention provide an ideal tool to detect rare mutations in detection of the presence and quantification of the amount of the rare nucleic acid changes. Therefore, applications for the methods of the present invention include, for example, early benign or malignant tumor detection, prenatal diagnostics particularly when using a blood sample from the mother, early viral or bacterial disease detection or detection of emerging strains of treatment resistant strains of bacteria or viruses in a target sample, environmental monitoring, monitoring of effects of pharmaceutical interventions such as early detection of multi drug resistance mutations in cancer treatment. The methods of the present invention are also useful in detection of rare mutant nucleic acid populations in mosaic organisms or individuals or one of their tissues composed of cells of more than one genotype, for example, in diagnosis of mitochondrial diseases or inherited diseases, wherein the mutation occurred after fertilization during early development of the embryo or fetus resulting in a mosaic genotype and consequently a mosaic phenotype.

The methods of the present invention are also useful in detection of rare mutations in inherited diseases which result in reduction of the transcript levels. It is sometimes easier to detect mutations from an RNA sample than from a genomic DNA sample. However, mutations causing significantly reduced transcript levels are often missed in these screens. The methods of the present invention can be used in detecting the known transcript reducing mutations which can be considered "rare mutations" because the mutant transcript population represents only a small percentage of the nucleic acids in the target sample.

Detection of rare mutations using the methods of the present invention also provide tools for forensic nucleic acid sample analysis by providing a system to reliably detect presence or absence of specific known nucleic acid polymorphisms to provide evidence, for example, to include or exclude crime suspects.

Additionally, the methods of the present invention are useful in detection of rare extremely virulent or dangerous mutations in biological agents, such as bacteria and viruses, that can be used as biological warfare agents. As the knowledge of dangerous mutations in viruses and/or bacteria increases, the present invention provides methods to detect small quantities of these abnormal mutants in a larger population of wildtype or less virulent agents.

The present invention also provides that the method can be modified for genotyping assays that might have an allele dropout problem. An allele dropout occurs when one allele is poorly amplified or detected, and a heterozygotic allele is mis-called as a homozygote. The dropout allele is often, but not always, the allele that produces a higher molecular weight base extension product.

For example, if the allele with the T base at the SNP (single nucleotide polymorphism) site is dropped out in a typical genotyping assay in the above presented example nucleic acid, the method according to the present invention provides that the use of ddTTP only, or ddTTP and much lower concentrations of other ddNTP/dNTP combinations, for the base extension reaction, will result in preferential extension of the 'dropped-out' allele, and therefore allele dropout is avoided.

The detection methods for detecting the primer extension products of the present invention can be any detection method which is capable of detecting the primer extension product after the primer extension reaction. If the dNTP or ddNTP is labeled with a detectable marker or reporter such as a fluorescent or radioactively label or some other detectable chemical group, the detection method is based on detecting the incorporation of the label into the primer extension product. Such detection methods include gel electrophoresis with laser detection or gel electrophoresis with detection of radioactivity, or other methods well known to one skilled in the art.

A "reporter molecule", as used herein, is a molecule which provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin, or radioisotopes. Commonly used enzymes include horseradish peroxidase, alkaline phosphatase, glucose oxidase and beta-galactosidase, among others. Enzymes can be conjugated to avidin or streptavidin for use with a biotinylated probe. Similarly, probes can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicylic acid or tolidine are commonly used. Incorporation of a reporter molecule into a DNA probe can be by any method known to the skilled artisan, for example by nick translation, primer extension, random oligo priming, by 3' or 5' end labeling or by other means (see, for example, Sambrook et al. *Molecular Biology: A laboratory Approach*, Cold Spring Harbor, N.Y. 1989).

Alternatively, the identified nucleic acids need not be labeled and can be used to quantitate allelic frequency using a mass spectrometry technique described in Ding C. and Cantor C. R., 2003, Proc. Natl. Acad. Sci. U.S.A. 100, 3059-64, which is herein incorporated by reference in its entirety.

The preferred method for detecting the primer extension products comprising the rare mutant nucleic acid is MALDI-TOF MS, using e.g. MASSARRAY™ system (Sequenom Inc., San Diego, Calif.).

In another embodiment, the invention provides a method of detecting nucleic acid molecules with a rare mutation comprising amplifying the nucleic acid sample with two primers that are designed to allele-specifically amplify the rare mutation containing nucleic acid, removing the excess dNTPs from the reaction after the amplification reaction, performing the primer extension reaction with only one dNTP or ddNTP, preferably dNPT, and a detection primer, which has been designed so that the 3' end is immediately adjacent to the mutation site, so that only the mutant nucleic acid will serve as a template to the primer extension reaction when the corresponding dNTP or ddNTP is used, and detecting the primer extension reaction product, wherein presence of the primer extension product after the primer extension reaction indicates the presence of a nucleic acid with a rare mutation.

In one embodiment, two reactions are performed using two different detection primers, wherein the first detection primer is designed to amplify the sense strand so that the 3' end of the primer anneals immediately adjacent to the mutation site in the sense strand and in the second reaction the detection primer is designed to amplify the antisense strand so that the 3' end of the primer anneals immediately adjacent to the mutation site in the antisense strand.

In yet another embodiment, the invention provides a method of quantification of nucleic acid molecules with rare mutations comprising the steps of amplifying a nucleic acid sample and a known amount of a control nucleic acid sample in the same reaction, wherein the control nucleic acid sample has been designed to have the same sequence as the rare mutation containing amplicon with the exception of one nucleic acid difference immediately adjacent to the mutation site. The amplification is performed with primers flanking the mutation site. After the amplification, the excess of dNTPs are removed and a primer extension reaction is performed using a detection primer, which is designed so that the 3' end of the primer anneals immediately adjacent to the rare mutation site. The detection reaction is performed in the presence of one deoxynucleotide (dNTP) and two dideoxynucleotides (ddNTPs): the dNTP corresponds to the first nucleoside after the 3' end of the detection primer in the nucleic acid with the rare mutation, the first ddNTP corresponds to the nucleoside artificially created to the control which differs from the nucleoside present in the rare mutant allele, and the second ddNTP corresponds to the nucleoside present in the rare mutant allele, preferably immediately after the mutation site. The primer extension products are then detected, and because the amount of the control originally added to the amplification reaction is known, the ratio of the control and the rare mutant containing nucleic acid molecules is used to determine the exact quantity of the mutant nucleic acid molecules in the sample.

The standard nucleic acid can be prepared using any method of nucleic acid synthesis know to one skilled in the art, including, for example, chemical oligonucleotide synthesis, by cloning and targeted mutagenesis, or by PCR with mutagenized primers.

Oligonucleotide primers or standards may be synthesized using methods well known in the art, including, for example, the phosphotriester (see Narang, S. A., et al., 1979, Meth. Enzymol., 68:90; and U.S. Pat. No. 4,356,270), phosphodiester (Brown, et al., 1979, Meth. Enzymol., 68:109), and phosphoramidite (Beaucage, 1993, Meth. Mol. Biol., 20:33) approaches. Each of these references is incorporated herein in its entirety by reference.

In one embodiment, rolling circle amplification (RCA) is used. Rolling circle amplification is an isothermal process for generating multiple copies of a sequence. In rolling circle DNA replication in vivo, a DNA polymerase extends a primer on a circular template (Komberg, A. and Baker, T. A. DNA Replication, W. H. Freeman, New York, 1991). The product consists of tandemly linked copies of the complementary sequence of the template. RCA is a method that has been adapted for use in vitro for DNA amplification (Fire, A. and Si-Qun Xu, Proc. Natl. Acad Sci. USA, 1995, 92:4641-4645; Lui, D., et al., J. Am. Chem. Soc., 1996, 118:1587-1594; Lizardi, P. M., et al., Nature Genetics, 1998, 19:225-232; U.S. Pat. No. 5,714,320 to Kool). RCA techniques are well known in the art, including linear RCA (LRCA). Any such RCA technique can be used in the present invention.

The methods of the present invention can be modified to utilize one or more control or competitor nucleic acids to quantify the amount of one or more rare mutant nucleic acid molecules in the same reaction.

The amount of the primer extension products is consequently measured by any of a variety of means, preferably by Mass Spectrometry (MALDI-TOF, or Matrix Assisted Laser Desorption Ionization-Time of Flight). In MALDI-TOF mass spectrometry, the peak area ratio between the products from the standard and the nucleic acid of interest comprising the rare mutation represents the ratio of the standard and the gene of interest. Since the concentration of the standard is known, the concentration of the nucleic acids with the rare mutation can be calculated.

Products of the primer extension reaction are detected and quantified using methods including, but not limited to, MALDI-TOF mass spectrometry, PYROSEQUENCING™, real time PCR, hybridization-based techniques, third wave invader assay, and fluorescence-based detection techniques.

In one preferred embodiment, the detection of the primer extension products in the methods of the present invention is performed using the MALDI-TOF mass spectrometry, using, for example the MASSARRAY™ system according to the manufacturer's instructions (Sequenom Inc., San Diego, Calif.).

Alternatively, an INVADER® assay can be used (Third Wave Technologies, Inc (Madison, Wis.)). This assay is generally based upon a structure-specific nuclease activity of a variety of enzymes, which are used to cleave a target-dependent cleavage structure, thereby indicating the presence of specific nucleic acid sequences or specific variations thereof in a sample (see, e.g. U.S. Pat. No. 6,458,535). For example, an INVADER® operating system (OS), provides a method for detecting and quantifying DNA and RNA. The INVADER® OS is based on a "perfect match" enzyme-substrate reaction. The INVADER® OS uses proprietary CLEAVASE® enzymes (Third Wave Technologies, Inc (Madison, Wis.)), which recognize and cut only the specific structure formed during the INVADER® process. The INVADER® OS relies on linear amplification of the signal generated by the INVADER® process, rather than on exponential amplification of the target. This allows quantification of target concentration.

In the INVADER® process, two short DNA probes hybridize to the target to form a structure recognized by the CLEAVASE® enzyme. The enzyme then cuts one of the probes to release a short DNA "flap." Each released flap binds to a fluorescently-labeled probe and forms another cleavage structure. When the CLEAVASE® enzyme cuts the labeled probe, the probe emits a detectable fluorescence signal.

In one embodiment, the primer extension products for the rare mutations are detected using PYROSEQUENCING™ (Uppsala, Sweden), which is essentially sequencing by synthesis. A sequencing primer, designed to anneal directly next to the nucleic acid differing between the rare and the common allele or the artificially produced quantification standard is first hybridized to a single stranded, PCR amplified, DNA template comprising both the target and the standard PCT product, and incubated with the enzymes, DNA polymerase, ATP sulfurylase, luciferase and apyrase, and the substrates, adenosine 5' phosphosulfate (APS) and luciferin. One of four deoxynucleotide triphosphates (dNTP), for example, corresponding to the nucleotide present in the standard template, is then added to the reaction. DNA polymerase catalyzes the incorporation of the dNTP into the standard DNA strand. Each incorporation event is accompanied by release of pyrophosphate (PPi) in a quantity equimolar to the amount of incorporated nucleotide. Consequently, ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated and allows determination of the amount of the standard nucleic acid sequence. Thereafter, apyrase, a nucleotide degrading enzyme, continuously degrades unincorporated dNTPs and excess ATP. When degradation is complete, another dNTP is added which corresponds to the dNTP present in the target template the amount of which is to be determined. Finally, addition of dNTPs is performed one at a time. Deoxyadenosine alfa-thio triphosphate (dATPαS) is used as a substitute for the natural deoxyadenosine triphosphate (dATP) since it is efficiently used by the DNA polymerase, but not recognized by the luciferase. Because the amount of the standard added in the PCR is known, the amount of the target can be calculated from the ratio of the incorporated dNTPs. For detailed information about reaction conditions, see, e.g. U.S. Pat. No. 6,210,891, which is herein incorporated by reference in its entirety.

The following illustrates quantification of concentration or copy numbers of rare alleles using the methods of the present invention. The sequence is the same example as above:

[SEQ ID NO: 12]
5'TGGGGCAAGGTGAACGTGGATGAAGTTGGTGGTGAGGCCCTGGGC

AGGTTaggggcagatagcagtga[A/T]{G/C}AGAGCGAGAGAGCCA

TCTATTGCTTACATTTGCTTCTGACACAACTGTGTTCACTAGCAACC

TCAAACAGACACCATGGTGCACCTGACTCCTGAGGAGAAGTCTGCCG

TTACTGCCCTG', wherein all the notations are the same as above, except the {G/C}. The G/C mutation is created to provide a detectable standard for the quantification reaction. In other words, a synthetic oligonucleotide with the sequence as the following GCAAGGTGAACGTGGATGAAGTTGGTG-GTGAGGCCCTGGGCAGGTTAGGGGCAG ATAG-CAGTGATCAGAGCGAGAGAGCCATCTAT-TGCTTACATTTGCTTCTGACACAACTG TGTTCAC-TAGCAACCTCAAACAGACACCATGGTGCACC [SEQ ID NO.: 3] is used as the internal standard for competitive PCR, wherein the bolded, underlined T represents the same nucleoside as in the rare mutant nucleic acid and the C is created to provide a detectable difference between the rare mutant and the standard.

The competitor carries the T base as the rare mutation at the natural polymorphic site. In addition, it also has a C base, instead of the G base, at the position next to the polymorphic site.

PCR, excess dNTP removal using, for example, shrimp alkaline phosphatase treatment, and consequently the base extension reaction are carried out. In the base extension reaction of the example, dTTP, ddGTP and ddCTP mixture is used. As a result, two extension products: aggggcagatagcagtgaTddG [SEQ ID NO.: 4] and aggggcagatagcagtgaTddC [SEQ ID NO.: 5] are produced. The first product comes from the rare mutation and the second product comes from the internal standard, the initial concentration of which is known. The ratio of the two products can be quantified by, for example, MALDI-TOF mass spectrometry, or other techniques, such as fluorescence measurement when ddCTP and ddGTP are tagged with different fluorescent groups.

Example 1

Detection and Quantification of Rare Mutation

Three DNA sequences including wildtype (wt), mutant (mut) and a competitor or the standard were used in this experiment. The sequences were:

```
WILDTYPE:
                                          [SEQ ID NO.: 6]
5'GTGGCAGATCTCTTCATGGTCTTCGGTGGCTTCACCACCAACCT
CTACACCTCTCTCCATGGGTACTTCGTCTTTGG-3'

MUTANT:
                                          [SEQ ID NO.: 7]
5'GTGGCAGATCTCTTCATGGTCTTCGGTGGCTTCACCACCATCCT
CTACACCTCTCTCCATGGGTACTTCGTCTTTGG-3'

COMPETITOR:
                                          [SEQ ID NO.: 8]
5'GTGGCAGATCTCTTCATGGTCTTCGGTGGCTTCACCACCATGCT
CTACACCTCTCTCCATGGGTACTTCGTCTTTGG-3'
```

The competitor was used as an internal standard for mut DNA quantification. Wt DNA is used as the background DNA which exist at a much higher concentration than mut DNA. The PCR primer sequences are: 5'ACGTTGGATGTGGCAGATCTCTTCATGGTC-3' [SEQ ID NO.: 9] and 5'ACGTTGGATGCCAAAGACGAAGTACCCATG-3' [SEQ ID NO.: 10]. The extension primer sequence was 5'CGGTGGCTTCACCACCA-3' [SEQ ID NO.: 11]. The extension ddNTP/dNTP mixture was dTTP/ddGTP/ddCTP.

Figure 1B:
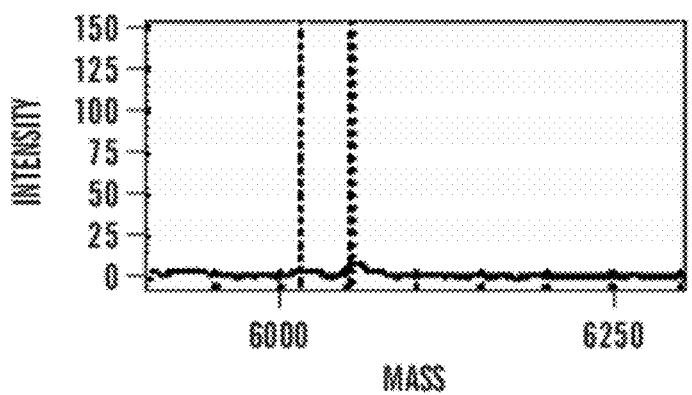
Figure 1C:
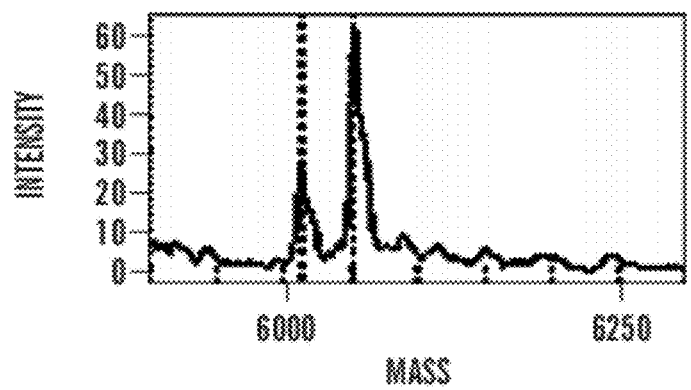
Figure 1D:
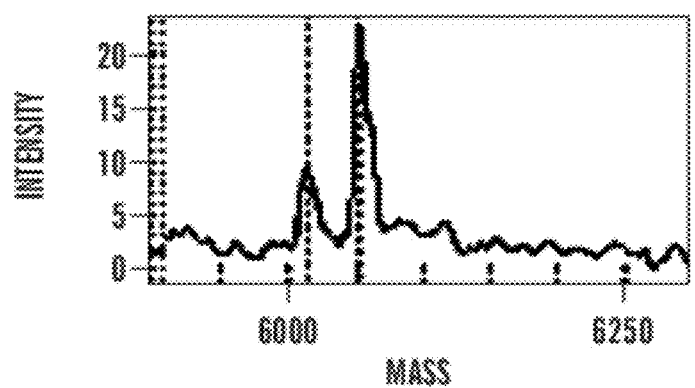
Figure 1E:
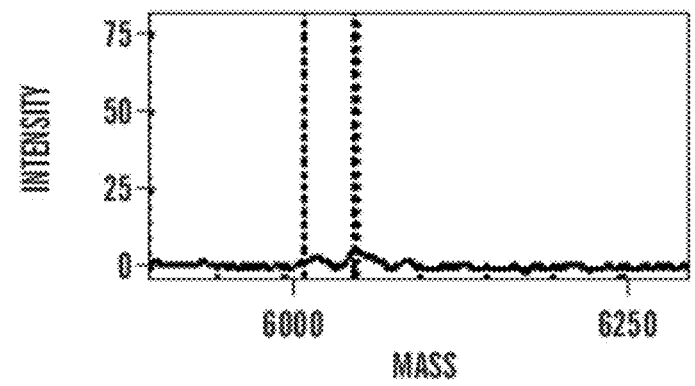

Different mixtures of the three DNAs were co-amplified by PCR. Excess dNTPs used in the PCR reaction were removed by shrimp alkaline phosphatase. Primer extension reaction was carried out using the extension primer and the extension ddNTP/dNTP mixture. FIGS. 1A-1E illustrate the results of the MALDI-TOF mass spectrometric analysis of the primer extension products. In the absence of wildtype DNA (FIG. 1A), 20 fold excess of wildtype DNA (FIG. 1C) and 100 fold excess of wildtype DNA (FIG. 1D), the ratios of mutant DNA and the competitor DNA are very similar which well exemplifies that the method of the present invention is capable of specifically amplifying the mutant allele and that the rare mutation can be enriched to provide an efficient detection and quantification method for detecting rare mutations in the presence of the much more common background nucleic acid variant. In FIG. 1B, only 500 fold excess wildtype DNA was present and neither mutant nor competitor DNA was present. The figure illustrates the specificity of the system to amplify only the rare mutant and the added standard, or competitor nucleic acid. In FIG. 1E, 500 fold excess wildtype DNA, mutant DNA and competitor DNA were all present.

Example 2

Matrix-assisted laser desorption ionization-time of flight mass spectrometry (MALDI-TOF MS) was adapted for quantitative gene expression analysis [1]. This technique, dubbed as real competitive PCR, combines competitive PCR, primer extension reaction and MALDI-TOF MS. After isolation of RNA and reverse transcription, cDNA is spiked with a synthetic oligonucleotide (the competitor) with an identical sequence except one single base roughly in the middle of the sequence to the cDNA of interest. The competitor and the cDNA of interest are co-amplified by PCR. Excess dNTPs are removed by shrimp alkaline phosphatase treatment after PCR. Then, a base extension reaction is carried out with an extension primer, a combination of three different ddNTPs and one dNTP and a ThermoSequenase. The base extension primer hybridizes right next to the mutation site and either one or two bases are added for the competitor and the cDNA, yielding two oligonucleotide products with different molecular weights (typically around 300 Da difference). In a typical molecular weight window of 4,000 to 9,000 Da, MALDI-TOF MS can easily distinguish two oligonucleotides if they differ by more than 10 Da. These two extension products are thus readily identified, and the ratio of their concentrations is quantified by MALDI-TOF MS.

Figure 2:
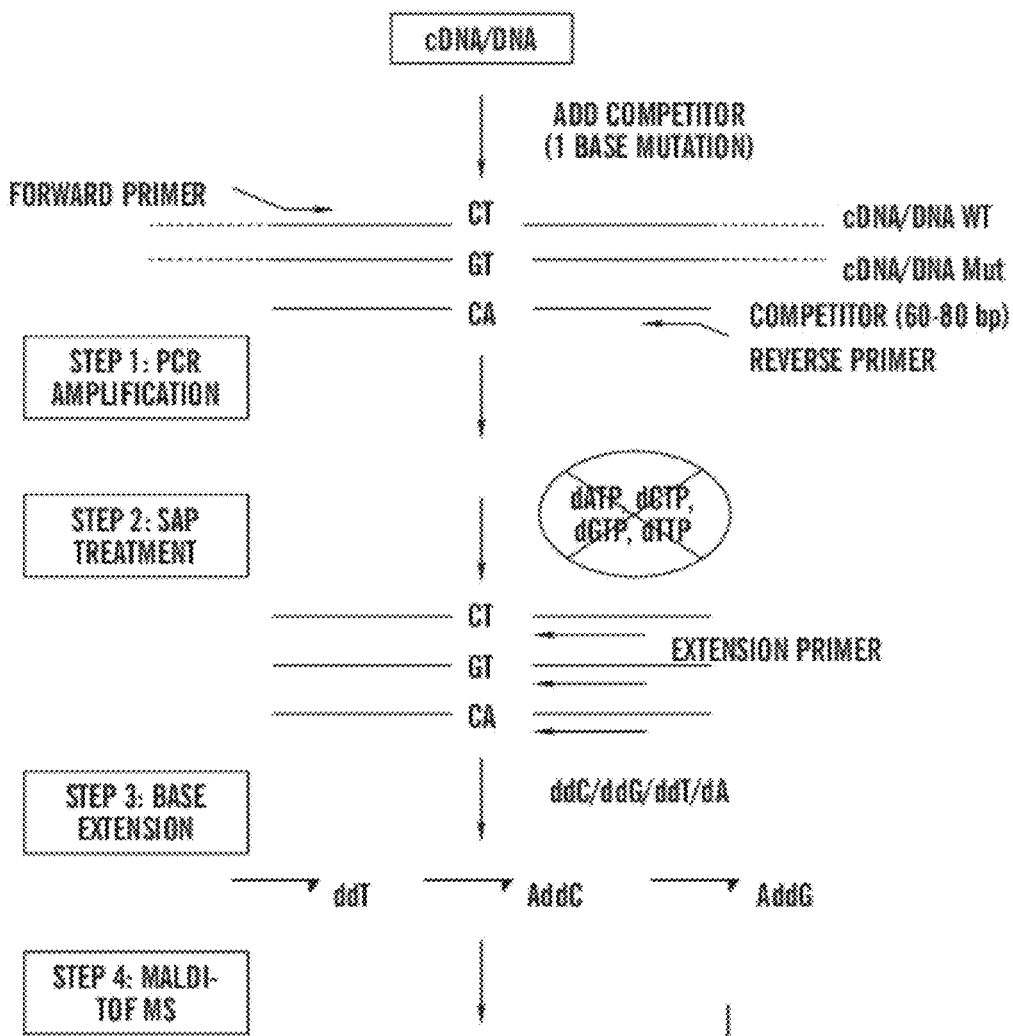
FIG. 2 shows a schematic view of quantitative and allele-specific expression analysis with real competitive PCR. A point mutation in the cDNA sequence is used as the marker for allele-specific gene expression analysis. The competitor is designed to have a synthetic mutation next to the natural mutation and is used for quantitative gene expression analysis. Three extension products from the two cDNA sequences and the competitor have different molecular weights, and are detected by MALDI-TOF MS. The peak area ratios of these products represent accurately the concentration ratios of the two cDNAs and the competitor. Since the absolute quantity of the competitor is known, the absolute quantities of the two cDNA sequences can be readily calculated.

As shown in FIG. 2, when the synthetic mutation created in the competitor is close to a natural mutation site in the cDNA sequence, real competitive PCR can be used for accurate allele-specific gene expression analysis. PCR is used to amplify the two cDNA sequences from the two alleles and the competitor. A base extension reaction with a mixture of three different ddNTPs and one dNTP is used to generate three (instead of two in a typical real competitive PCR experiment) oligonucleotides for the two cDNAs and the competitor. The three products are identified and their ratios are calculated based on their peak areas in the mass spectrum.

Since the amount of competitor spiked in is known, the absolute concentration of each of the two cDNAs can be easily calculated. Thus, it is possible to simultaneously quantify the gene expression levels from the two alleles of one gene. The competitor and the two cDNAs are virtually identical in sequence and are amplified with the same kinetics. The allele specificity is superior due to the high precision of MALDI-TOF MS in molecular weight determination.

One example of allele-specific expression analysis by real competitive PCR is shown in FIG. 3A. A single nucleotide polymorphism (refSNP ID: rs2069849) located in exon 2 of the interleukin 6 gene is selected as the marker for allele-specific expression. Complementary DNA (0.025 ng) prepared from the IMR-90 cell line (ATCC) was co-amplified with $5 \times 10^{-22}$ Mol (301 copies) of the competitor. The oligonucleotide products from the base extension reaction were analyzed by MALDI-TOF MS. The peak area ratios represent accurately the concentration ratios of the two cDNAs and the competitor. Coefficient of variations (CV is defined as standard deviation divided by the mean) for the relative frequencies of the three peaks were 9.2%, 4.1% and 4.4% for four real competitive PCR replicates, indicating excellent precision. The interleukin 6 gene also shows modest skewing in allelic expression (98 copies of C allele was expressed, and 136 copies of T allele was expressed, see FIG. 3A).

We next tested allele-specific expression of the lexA gene in *Escherichia coli*. Gene expression perturbation in *E. coli* was used for gene network studies [2]. Expression perturbation was achieved by introducing an exogenous copy for each gene of interest in an inducible expression plasmid. The expression of each gene potentially in a gene regulatory network was perturbed via the induction of the exogenous gene expression, and the expression changes of other genes were analyzed. These perturbed gene expression levels were then fed into a multiple linear regression algorithm to estimate the network interactions. This approach is a powerful tool for functional genomics analysis. However, self-regulatory interactions such as positive and negative self-feedbacks can only be resolved by measuring the exogenous and endogenous gene expression separately. In the original study on the *E. coli* network, a reporter gene (luciferase), expressed under identical conditions as the gene of interest, was used to estimate the exogenous gene expression. However, this estimate is likely to be inaccurate since the expression level of the luciferase gene is likely to be different from the exogenous genes, even when they are under the control of the same promoter. A method to directly and separately quantify the expressions of the exogenous and the endogenous gene is needed to obtain significantly more accurate estimates of self-regulatory interactions in gene networks.

To this end, an exogenous lexA was introduced into *E. coli* via the pBADX53 vector. The exogenous lexA gene is distinguishable from the endogenous lexA gene by a silent mutation (TCC to TCG silent mutation at codon 103). The exogenous lexA expression was induced with arabinose. Without arabinose, only endogenous lexA transcript was detected (FIG. 3B). With an intermediate arabinose induction, exogenous lexA was expressed at about 20% level compared with the endogenous lexA (FIG. 3B).

Example 3

Figure 3C:
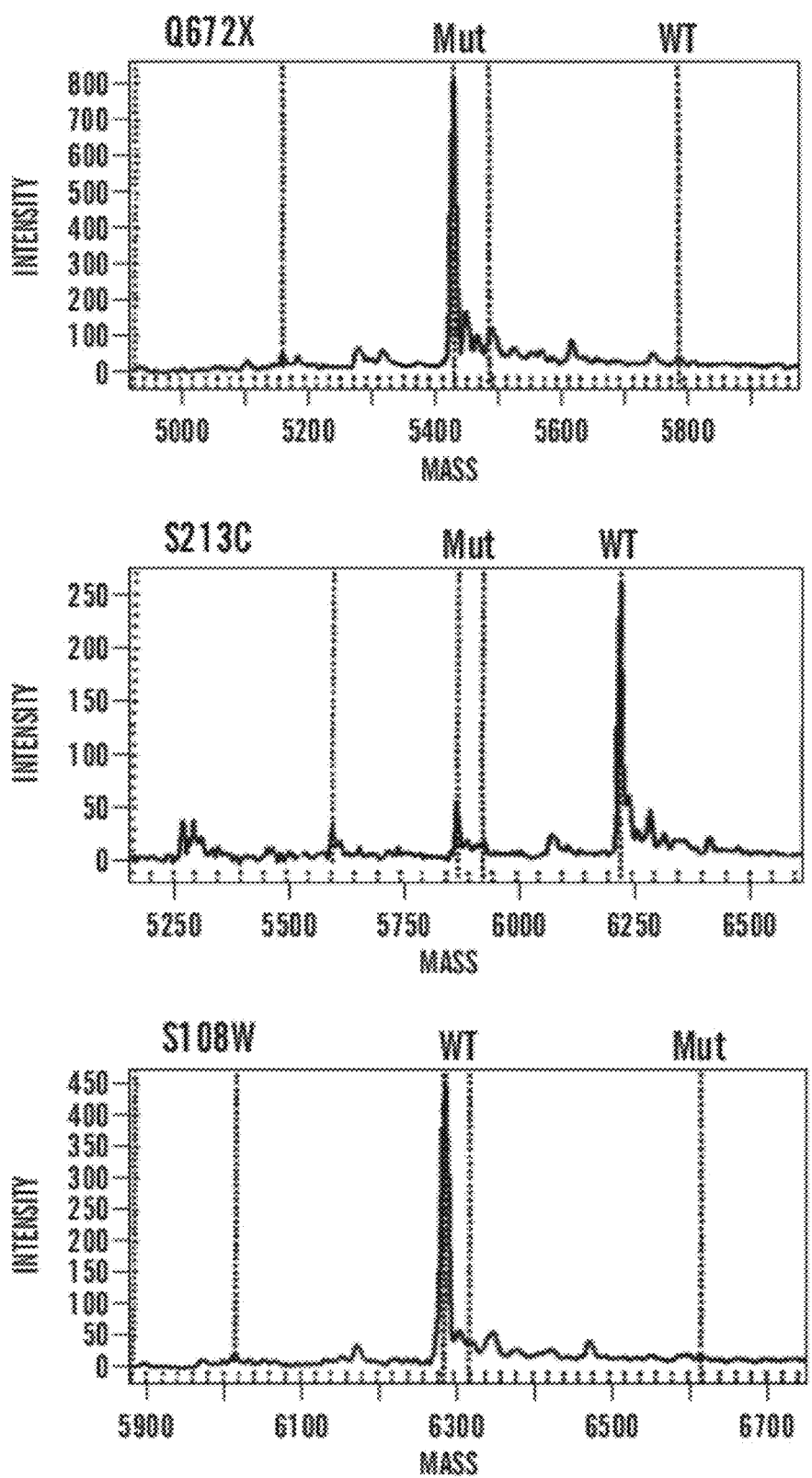
FIG. 3 shows a mass spectra for allele-specific expression analysis. (A) Interleukin 6 gene. Peaks are identified by C, T and S. C represents the allele where the polymorphic site has a C residue. T represents the allele where the polymorphic site has a T residue. S represents the competitor. The peak areas of C, T and S peaks are automatically computed by the RT software package (SEQUENOM). The peak area ratios represent the concentration ratios of the starting cDNA sequences and the competitor. The peak frequencies are 0.209, 0.263 and 0.528 for peak C, T and S, respectively. (B) lexA gene. Peak S, G and C represent the competitor, the exogenous and the endogenous lexA gene, respectively. Without arabinose induction, only endogenous lexA gene expression was seen. With modest arabinose induction, both the endogenous and exogenous lexA gene expression were seen. Without induction, the peak frequencies are 0.601, 0.004 and 0.395 for peak S, G and C, respectively. With induction, the peak frequencies are 0.509, 0.075 and 0.416 for peak S, G and C, respectively. (C) ABCD-1 gene. Mut and WT represent mutant and wildtype alleles, respectively. For Q672X, the peak frequencies are 0.984 and 0.016 for peak Mut and WT, respectively. For S213C, the peak frequencies are 0.187 and 0.813 for peak Mut and WT, respectively. For S108W, the peak frequencies are 0.995 and 0.005 for peak WT and Mut, respectively.

In the third example, we tested allele-specific expression of the ABCD-1 gene (located on the X chromosome) involved in X-linked adrenoleukodystrophy (XALD). The manifestation of symptoms in XALD carriers was previously shown to be associated with a higher degree of non-random X chromosome inactivation [3]. A non-random X chromosome inactivation is likely to cause a preferential expression down-regulation of one of the ABCD-1 allele. If the wildtype allele is inactivated, the mutant allele will be predominantly expressed. Thus, the individual might show symptoms similar to a homozygous mutant. X chromosome inactivation studies can only provide a genome-wide, indirect picture while direct allele-specific gene expression can provide the direct link between gene expression and disease manifestation. We thus carried out allele-specific gene expression for three carriers with three different ABCD-1 mutations (S108W, S213C and Q672X). The S108W carrier showed predominant (>99%) mutant allele expression while the S213C and Q672X showed predominant wildtype allele (89% and >99%, respectively) expression (FIG. 3C). This result is in complete concordance with results obtained previously [3].

These examples demonstrate quantitative and allele-specific gene expression analysis with real competitive PCR. The allele specificity for gene expression analysis used is the superior molecular weight determination ability of the MALDI-TOF MS technology. Highly precise (CV 4%-9%) and absolute gene expression analysis is achieved. In addition, the real competitive PCR used the highly automated MassARRAY system (SEQUENOM), and is ideal for high-throughput (7000 reactions/day/instrument) analysis. The high-throughput and low cost features of this technique can easily be exploited in large-scale allele-specific expression studies.

Materials and Methods
    cDNA and Oligonucleotides
    Interleukin 6 Gene Expression Analysis
    Complementary DNA for interleukin 6 gene expression analysis was prepared from cell line IMR-90 (ATCC). The PCR primer sequences for the interleukin 6 gene expression analysis are:

```
                                          [SEQ ID NO: 13]
   5'-ACGTTGGATGGCAGGACATGACAACTCATC-3'
   and

[SEQ ID NO: 14]
   5'-ACGTTGGATGCCATGCTACATTTGCCGAAG-3'.
```

The extension primer sequence is 5'-CGCAGCTTTAAG-GAGTT-3' [SEQ ID NO: 15]. The synthetic competitor sequence is 5'-GCCCATGCTACATTTGCCGAAGAGC-CCTCAGGCTGGACTGCATAAACTCCTTAAAGCTG CGCAGAATGAGATGAGTTGTCATGTCCTGCAG-3' [SEQ ID NO: 16]. All oligonucleotides were purchased from Integrated DNA Technologies (Coralville, Iowa). The synthetic competitor was PAGE purified by the vendor and absorbance at 260 nm was measured in our laboratory.

lexA Gene Expression Analysis

RNA samples for lexA gene expression analysis were provided by Dr. Timothy Gardner (Boston University). The exogenous lexA gene has a TCC to TCG silent mutation at codon 103 so that it can be distinguished from the endogenous lexA gene. The exogenous lexA gene was cloned in the vector pBADX53. Bacterial culture and RNA extraction were carried out as previously described [10]. The PCR primer sequences for the lexA gene expression analysis are, 5'-ACGTTGGATGGCGCAACAGCATATTGAAGG-3' [SEQ ID NO: 17] and 5'-ACGTTGGATGACATCCCGCT-GACGCGCAGC-3' [SEQ ID NO: 18]. The extension primer sequence is 5'-ATCAGCATTCGGCTTGAATA-3' [SEQ ID NO: 19]. The synthetic competitor sequence is 5'-ACATC-CCGCTGACGCGCAGCAGGAAATCAGCAT-TCGGCTTGAATATGGAAGGATCGAC CTGATAAT-GACCTTCAATATGCTGTTGCGC-3' [SEQ ID NO: 20]. The synthetic competitor was PAGE purified by the vendor and absorbance at 260 nm was measured in our laboratory.

ABCD-1 Gene Expression Analysis

Complementary DNA and genomic DNA samples for ABCD-1 gene expression analysis were prepared as previously described [11]. Three ABCD-1 carriers, S108W, S213C and Q672X, were used in this study. PCR primers for the three mutations are: 5'-ACGTTGGATGAGCAGCTGCCAGC-CAAAAGC-3' [SEQ ID NO: 21] and 5'-ACGTTGGAT-GACTCGGCCGCCTTGGTGAG-3' [SEQ ID NO: 22] for S108W, 5'-ACGTTGGATGTAGGAAGTCACAGC-CACGTC-3' [SEQ ID NO: 23] and 5'-ACGTTGGATGAAC-CCTGACCAGTCTCTGAC-3' [SEQ ID NO: 24] for S213C, and 5'-ACGTTGGATGTCCCTGTGGAAATACCACAC-3' [SEQ ID NO: 25] and 5'-ACGTTGGATGAGTCCAGCT-TCTCGAACTTC-3' [SEQ ID NO: 26] for Q672X. The extension primers are: 5'-GGCGGGCCACATACACC-3' [SEQ ID NO: 27] for S108W, 5'-AGTGGCTTGGTCAG-GTTG-3' [SEQ ID NO: 28] for S213C and 5'-AATACCACA-CACACTTGCTA-3' [SEQ ID NO: 29] for Q672X.

Real Competitive PCR

Real competitive PCR was carried out as was previously described [9].

Step 1: PCR Amplification

Each PCR reaction contains 1 μL diluted cDNA (0.025 ng/μL), 0.5 μL 10× HotStar Taq PCR buffer, 0.2 μL, MgCl$_2$ (25 mM), dNTP mix (25 mM each), 0.02 μL HotStar Taq Polymerase (50 U/μL, Qiagen), 0.1 μL, competitor oligonucleotide (5×10$^{-9}$ μM), 10 μL forward and reverse primer (1 μM each) and 2.14 μL ddH$_2$O. The PCR condition was: 95° C. for 15 min for hot start, followed by denaturing at 94° C. for 20 sec, annealing at 56° C. for 30 sec and extension at 72° C. for 1 min for 45 cycles, and finally incubated at 72° C. for 3 min.

Step 2: Shrimp Alkaline Phosphatase Treatment

PCR products were treated with shrimp alkaline phosphatase to remove excess dNTPs. A mixture of 0.17 μL hME buffer (SEQUENOM), 0.3 μL shrimp alkaline phosphatase (SEQUENOM) and 1.53 μL ddH$_2$O was added to each PCR reaction. The reaction solutions (now 7 μL each) were incubated at 37° C. for 20 min, followed by 85° C. for 5 min to inactive the enzyme.

Step 3: Single Base Extension Reaction

For each base extension reaction, 0.2 μL of selected ddNTPs/dNTP mixture (SEQUENOM), 0.108 μL of selected extension primer, 0.018 μL of ThermoSequenase (32 U/μL, SEQUENOM) and 1.674 μL ddH$_2$O were added. The base extension condition was, 94° C. for 2 min, followed by 94° C. for 5 sec, 52° C. for 5 sec and 72° C. for 5 sec for 40 cycles. The ddNTPs/dNTP mixtures are: ddATP/ddCTP/ddGTP/dTTP for interleukin 6 and ABCD-1 Q672X, ddTTP/ddCTP/ddGTP/dATP for lexA, and ddATP/ddCTP/ddTTP/dGTP for ABCD-1 S108W and S213C.

Step 4: Liquid Dispensing and MALDI-TOF MS

The final base extension products were treated with SpectroCLEAN (SEQUENOM) resin to remove salts in the reaction buffer. This step was carried out with a Multimek (Beckman) 96 channel auto-pipette and 16 μL resin/water solution was added into each base extension reaction, making the total volume 25 μL. After a quick centrifugation (2,500 rpm, 3 min) in a Sorvall legend RT centrifuge, approximately 10 nL of reaction solution was dispensed onto a 384 format SpectroCHIP (SEQUENOM) pre-spotted with a matrix of 3-hydroxypicolinic acid (3-HPA) by using a MassARRAY Nanodispenser (SEQUENOM). A modified Bruker Biflex MALDI-TOF mass spectrometer was used for data acquisitions from the SpectroCHIP. Mass spectrometric data were automatically imported into the SpectroTYPER (SEQUENOM) database for automatic analysis such as noise normalization and peak area analysis.

REFERENCES

1. Ding C, Cantor C R. A high-throughput gene expression analysis technique using competitive PCR and matrix-assisted laser desorption ionization time-of-flight MS. Proc Natl Acad Sci USA 2003; 100:3059-3064.
2. Gardner T S, di Bernardo D, Lorenz D, Collins J J. Inferring genetic networks and identifying compound mode of action via expression profiling. Science 2003; 301:102-105.
3. Maier E M, Kammerer S, Muntau A C, Wichers M, Braun A, Roscher A A. Symptoms in carriers of adrenoleukodystrophy relate to skewed X inactivation. Ann Neurol 2002; 52:683-688.

The above-cited references and those reference cited throughout the specification are herein incorporated by reference in their entirety.

What is claimed is:

1. A method of detecting the presence of one or more nucleic acids with a rare mutation in a sample, wherein said rare mutation includes any change from a wildtype sequence including polymorphisms that are present in less than 10% of the nucleic acid molecules in the sample, comprising the steps of:
   (a) providing a nucleic acid sample comprising a mixture of nucleic acids wherein the mixture of nucleic acids comprises at least one nucleic acid with a rare mutation that is present in less than 10% of nucleic acids in the sample;
   (b) in an amplification reaction amplifying the nucleic acid sample with primers flanking the sequence carrying the rare mutation, wherein the primers allele-specifically amplify the nucleic acid with the rare mutation;
   (c) removing excess dNTPs after the amplification reaction;
   (d) performing a primer extension reaction using (i) one or more detection primers which are designed so that the 3' end of the detection primer is immediately adjacent to a nucleic acid which differentiates the rare mutation carrying nucleic acid from a wildtype nucleic acid molecule, and (ii) only one dNTP or only one ddNTP selected according to the rare mutation, wherein the dNTP or the ddNTP corresponds to a nucleoside adjacent to the detection primer in the nucleic acids with the rare mutation; and
   (e) detecting the presence of the primer extension product(s) after the primer extension reaction and/or detecting the consumption of the dNTP or the ddNTP,
wherein the presence of a primer extension product in the reaction or the consumption of the dNTP or the ddNTP indicates the presence of the nucleic acid with a rare mutation.

2. The method of claim 1, wherein the detected primer extension product is further quantified.

3. The method of claim 1, wherein the primer extension product is quantified using MALDI-TOF mass spectrometry.

4. The method of claim 1, wherein the mixture of nucleic acids in step (a) is suspected to comprise less than 1% of nucleic acids with the rare mutation.

5. The method of claim 1, wherein parallel primer extension reactions are performed using two different detection primers, wherein a first detection primer is designed so that the 3' end of the first detection primer anneals immediately adjacent to the mutation site in the sense strand and in a second reaction a second detection primer is designed so that the 3' end of the second detection primer anneals immediately adjacent to the mutation site in the antisense strand.

6. A method of detecting the presence of one or more nucleic acids with a rare mutation in a sample, wherein said rare mutation includes any change from a wildtype sequence including polymorphisms that are present in less than 10% of the nucleic acid molecules in the sample, comprising the steps of:
 (a) providing a nucleic acid sample comprising a mixture of nucleic acids wherein the mixture of nucleic acids comprises at least one nucleic acid with a rare mutation that is present in less than 10% of nucleic acids in the sample;
 (b) in an amplification reaction amplifying the nucleic acid sample with primers flanking the sequence carrying the rare mutation, wherein the primers allele-specifically amplify the nucleic acid with the rare mutation;
 (c) removing excess dNTPs after the amplification reaction;
 (d) performing a primer extension reaction using (i) one or more detection primers which are designed so that the 3' end of the detection primer is immediately adjacent to a nucleic acid which differentiates the rare mutation carrying nucleic acid from a wildtype nucleic acid molecule, and (ii) only one dNTP or only one ddNTP selected according to the rare mutation, wherein the dNTP or the ddNTP corresponds to a nucleoside adjacent to the detection primer in the nucleic acids with the rare mutation; and
 (e) detecting the consumption of the dNTP or the ddNTP, wherein the consumption of the dNTP or the ddNTP indicates the presence of the nucleic acid with a rare mutation and, wherein the consumption of dNTP or the ddNTP is detected using pyrosequencing.

7. A method of detecting and quantifying one or more nucleic acids with a rare mutation in a sample, wherein said rare mutation includes any change from a wildtype nucleic acid sequence, including polymorphisms, that are present in less than 10% of the nucleic acid molecules in the sample, comprising the steps of:
 (a) providing a nucleic acid sample comprising a mixture of nucleic acids wherein the mixture of nucleic acids comprises at least one nucleic acid with a rare mutation that is present in less than 10% of the nucleic acid molecules in the sample;
 (b) adding to the nucleic acid sample a known amount of an artificial competitor nucleic acid which differs from the nucleic acid with the rare mutation by one nucleotide immediately adjacent to the mutation;
 (c) amplifying the nucleic acid with a pair of primers capable of amplifying the nucleic acid with the rare mutation and the artificial competitor nucleic acid, wherein the pair of primers flank the mutation;
 (d) removing excess dNTPs after the amplification reaction;
 (e) performing a primer extension reaction using one or more detection primers which are designed so the 3' end of the detection primer is immediately adjacent to the mutation, wherein the primer extension reaction comprises a combination of dNTPs and/or ddNTPs which:
  (i) permits extension of a detection primer hybridized to the amplified nucleic acid with the rare mutation;
  (ii) permits extension of a detection primer hybridized to the amplified artificial competitor nucleic acid;
  (iii) does not permit extension of any detection primer hybridized to the wildtype nucleic acid sequence; and
  (iv) wherein the detection primer extension products of (i) and (ii) are different;
 (f) comparing the amounts of the detection primer extension products of (i) and (ii) to quantify the nucleic acid with the rare mutation based on the known amount of artificial competitor nucleic acid.

8. The method of claim 7, wherein the quantifying is performed using MALDI-TOF mass spectrometry.

* * * * *

SEQUENCE LISTING

```
<160> NUMBER OF SEQ ID NOS: 29

<210> SEQ ID NO 1
<211> LENGTH: 190
<212> TYPE: DNA
<213> ORGANISM: Unknown
<220> FEATURE:
<223> OTHER INFORMATION: Description of Unknown: Hypothetical nucleic
      acid molecule sequence

<400> SEQUENCE: 1
tggggcaagg tgaacgtgga tgaagttggt ggtgaggccc tgggcaggtt aggggcagat      60
agcagtgawg agagcgagag agccatctat tgcttacatt tgcttctgac acaactgtgt     120
tcactagcaa cctcaaacag acaccatggt gcacctgact cctgaggaga agtctgccgt     180
tactgccctg                                                           190

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggggcagat agcagtgat                                                   19

<210> SEQ ID NO 3
```

-continued

```
<211> LENGTH: 151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gcaaggtgaa cgtggatgaa gttggtggtg aggccctggg caggttaggg gcagatagca    60
gtgatcagag cgagagagcc atctattgct tacatttgct tctgacacaa ctgtgttcac   120
tagcaacctc aaacagacac catggtgcac c                                  151

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aggggcagat agcagtgatg                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aggggcagat agcagtgatc                                                20

<210> SEQ ID NO 6
<211> LENGTH: 77
<212> TYPE: DNA
<213> ORGANISM: Unknown
<220> FEATURE:
<223> OTHER INFORMATION: Description of Unknown: Hypothetical nucleic
      acid molecule sequence

<400> SEQUENCE: 6
gtggcagatc tcttcatggt cttcggtggc ttcaccacca acctctacac ctctctccat    60
gggtacttcg tctttgg                                                   77

<210> SEQ ID NO 7
<211> LENGTH: 77
<212> TYPE: DNA
<213> ORGANISM: Unknown
<220> FEATURE:
<223> OTHER INFORMATION: Description of Unknown: Hypothetical nucleic
      acid molecule sequence

<400> SEQUENCE: 7
gtggcagatc tcttcatggt cttcggtggc ttcaccacca tcctctacac ctctctccat    60
gggtacttcg tctttgg                                                   77

<210> SEQ ID NO 8
<211> LENGTH: 77
<212> TYPE: DNA
<213> ORGANISM: Unknown
<220> FEATURE:
<223> OTHER INFORMATION: Description of Unknown: Hypothetical nucleic
      acid molecule sequence
```

<400> SEQUENCE: 8
gtggcagatc tcttcatggt cttcggtggc ttcaccacca tgctctacac ctctctccat    60
gggtacttcg tctttgg                                                  77

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgttggatg tggcagatct cttcatggtc                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgttggatg ccaaagacga agtacccatg                                    30

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cggtggcttc accacca                                                  17

<210> SEQ ID NO 12
<211> LENGTH: 190
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tggggcaagg tgaacgtgga tgaagttggt ggtgaggccc tgggcaggtt aggggcagat    60
agcagtgaws agagcgagag agccatctat tgcttacatt tgcttctgac acaactgtgt   120
tcactagcaa cctcaaacag acaccatggt gcacctgact cctgaggaga agtctgccgt   180
tactgccctg                                                         190

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgttggatg gcaggacatg acaactcatc                                    30

```
<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acgttggatg ccatgctaca tttgccgaag                                        30

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgcagcttta aggagtt                                                      17

<210> SEQ ID NO 16
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcccatgcta catttgccga agagccctca ggctggactg cataaactcc ttaaagctgc       60
gcagaatgag atgagttgtc atgtcctgca g                                      91

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttggatg gcgcaacagc atattgaagg                                        30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgttggatg acatcccgct gacgcgcagc                                        30

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atcagcattc ggcttgaata                                                   20
```

```
<210> SEQ ID NO 20
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
acatcccgct gacgcgcagc aggaaatcag cattcggctt gaatatggaa ggatcgacct    60
gataatgacc ttcaatatgc tgttgcgc                                       88

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgttggatg agcagctgcc agccaaaagc                                     30

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgttggatg actcggccgc cttggtgag                                      29

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acgttggatg taggaagtca cagccacgtc                                     30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgttggatg aaccctgacc agtctctgac                                     30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgttggatg tccctgtgga aataccacac                                     30
```

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acgttggatg agtccagctt ctcgaacttc                                      30

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcgggccac atacacc                                                    17

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtggcttgg tcaggttg                                                   18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aataccacac acacttgcta                                                 20